United States Patent
Engdahl et al.

(10) Patent No.: US 7,345,474 B2
(45) Date of Patent: *Mar. 18, 2008

(54) DETECTOR FOR MAGNETIZABLE MATERIAL USING AMPLITUDE AND PHASE DISCRIMINATION

(75) Inventors: Jonathan R. Engdahl, Chardon, OH (US); Ira B. Goldberg, Thousand Oaks, CA (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/179,959

(22) Filed: Jul. 12, 2005

(65) Prior Publication Data

US 2005/0252981 A1    Nov. 17, 2005

Related U.S. Application Data

(63) Continuation of application No. 10/012,939, filed on Dec. 10, 2001, now Pat. No. 6,937,011.

(51) Int. Cl.
*G01N 27/72* (2006.01)
*G01R 33/12* (2006.01)

(52) U.S. Cl. .................................. 324/233
(58) Field of Classification Search .............. 53/445, 53/474; 324/233, 207.21, 252, 207.13, 239, 324/227
See application file for complete search history.

(56) References Cited

U.S. PATENT DOCUMENTS

| | | | |
|---|---|---|---|
| 3,401,129 A * | 9/1968 | McGinley | ................ 524/524 |
| 4,215,342 A | 7/1980 | Horowitz | |
| 4,309,697 A | 1/1982 | Weaver | |
| 4,915,728 A | 4/1990 | Schell | |
| 5,051,726 A | 9/1991 | Copeland et al. | |
| 5,103,234 A | 4/1992 | Watkins et al. | |
| 5,239,696 A | 8/1993 | Balch et al. | |
| 5,387,900 A | 2/1995 | Plonsky et al. | |
| 5,396,999 A * | 3/1995 | Sandheinrich | .............. 206/542 |
| 5,414,410 A | 5/1995 | Davies et al. | |
| 5,576,693 A | 11/1996 | Tyren et al. | |
| 5,632,237 A | 5/1997 | Cornell et al. | |
| 5,664,582 A | 9/1997 | Szymaitis | |
| 5,834,748 A | 11/1998 | Litman | |
| 5,988,500 A | 11/1999 | Litman | |
| 6,053,406 A | 4/2000 | Litman | |
| 6,079,778 A | 6/2000 | Lindberg | |
| 6,278,368 B1 * | 8/2001 | Goldberg et al. | ........ 340/572.4 |
| 6,788,049 B2 * | 9/2004 | Engdahl et al. | ............. 324/233 |
| 6,937,011 B2 * | 8/2005 | Engdahl et al. | ............. 324/233 |

FOREIGN PATENT DOCUMENTS

| | | |
|---|---|---|
| GB | 2210235 A | 6/1989 |
| WO | WO 95/18430 | 7/1995 |
| WO | WO 98/26377 | 6/1998 |
| WO | WO 98/26378 | 6/1998 |
| WO | WO 98/26379 | 6/1998 |

* cited by examiner

*Primary Examiner*—Reena Aurora
(74) *Attorney, Agent, or Firm*—Keith M. Baxter; William R. Walbrun

(57) ABSTRACT

A detector for magnetizable materials operates remotely to determine a amplitude and phase modification of an exciting magnetic field caused by the magnetizable materials. These amplitude and phase measurements are used to create a phase-amplitude trajectory in phase amplitude space, which may be finely divided to distinguish among a number of different types of components.

14 Claims, 8 Drawing Sheets

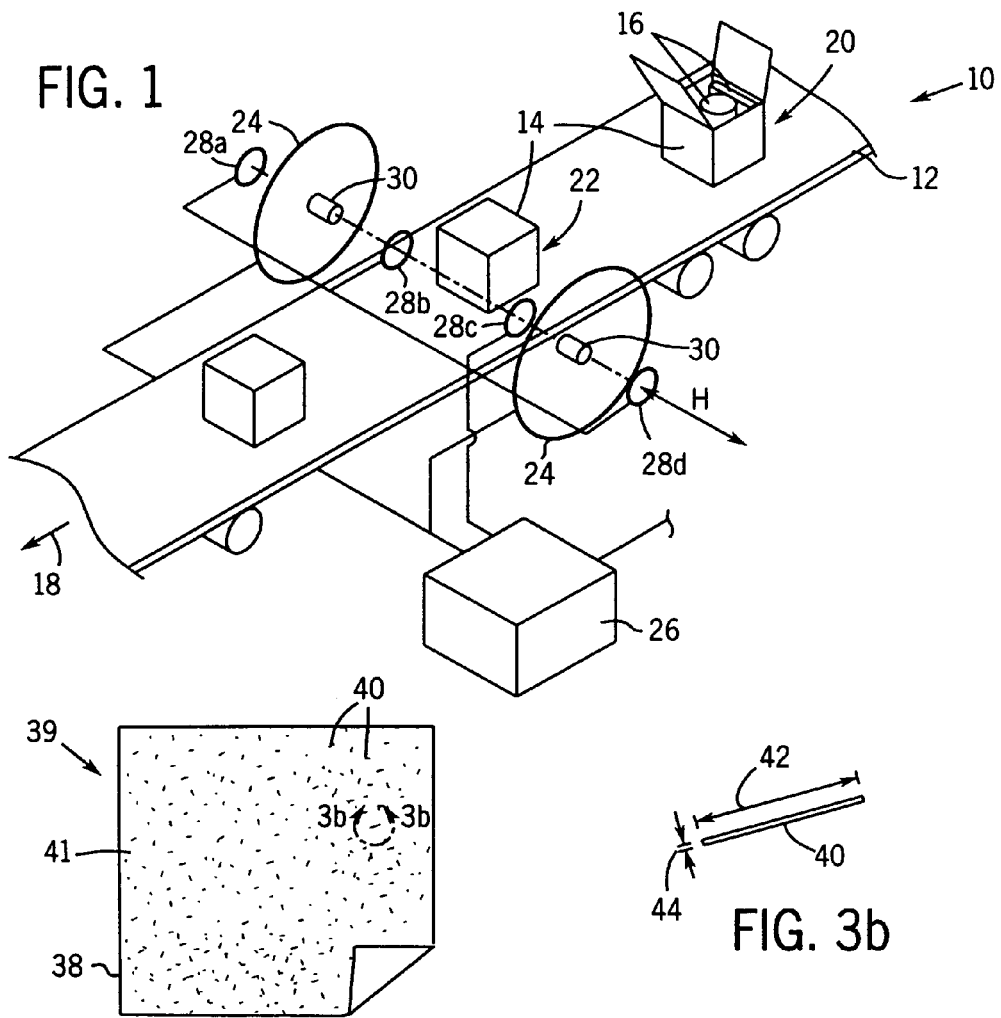
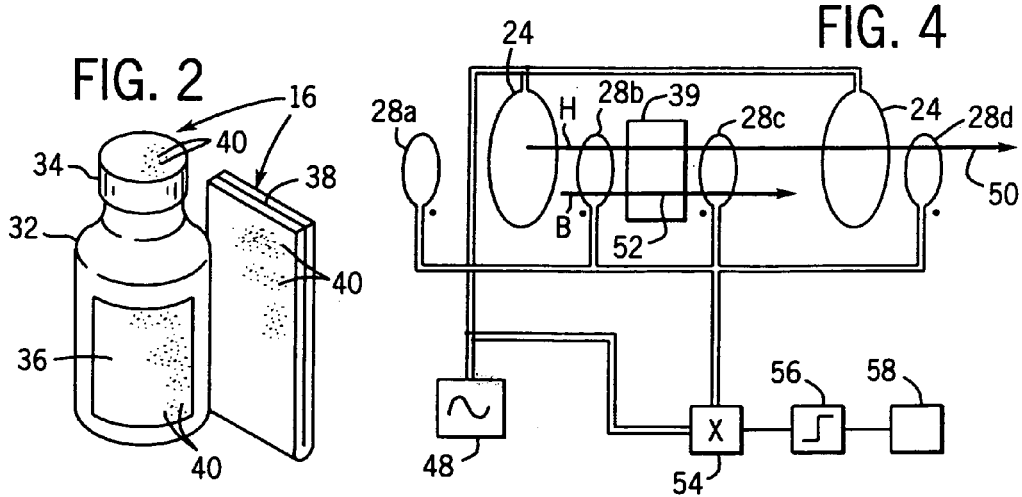

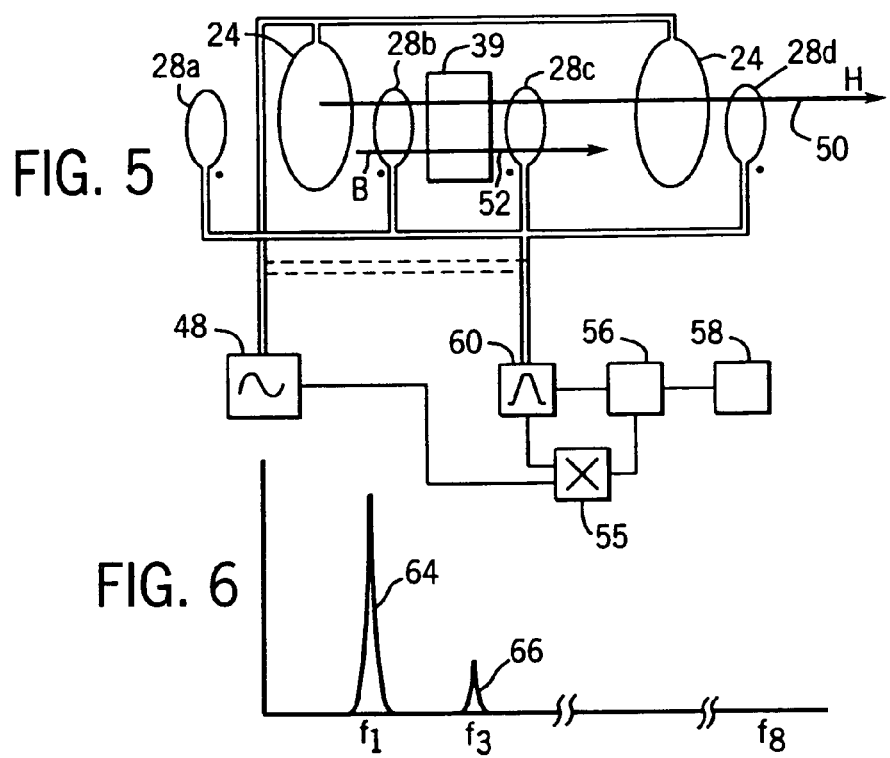
FIG. 5
FIG. 6
FIG. 7
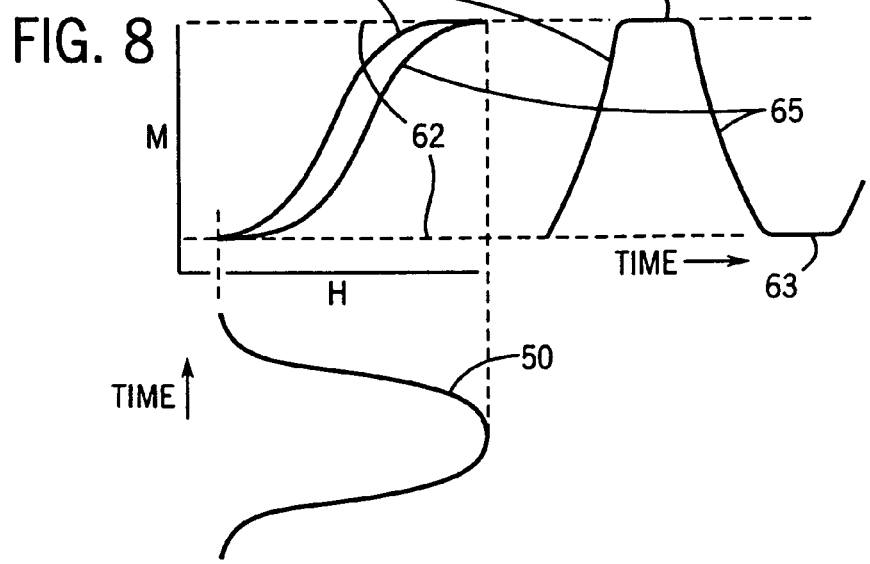
FIG. 8

- ● — SS304
- ▲ — SS304, HiMu80
- ✕ — SS204, HiMu80, FeCr ALLOY

FIG. 15
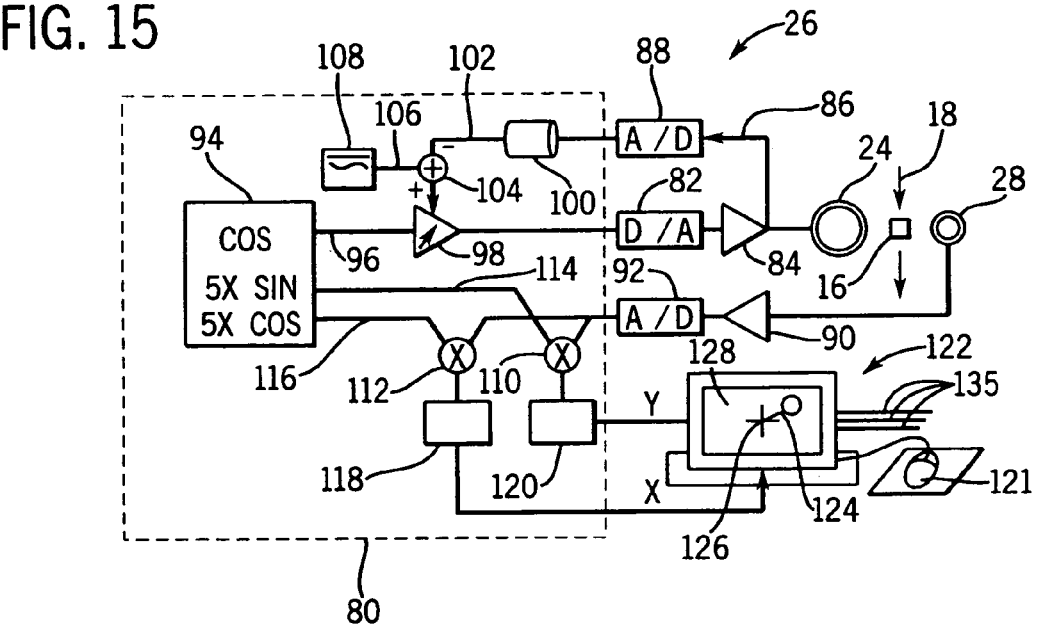
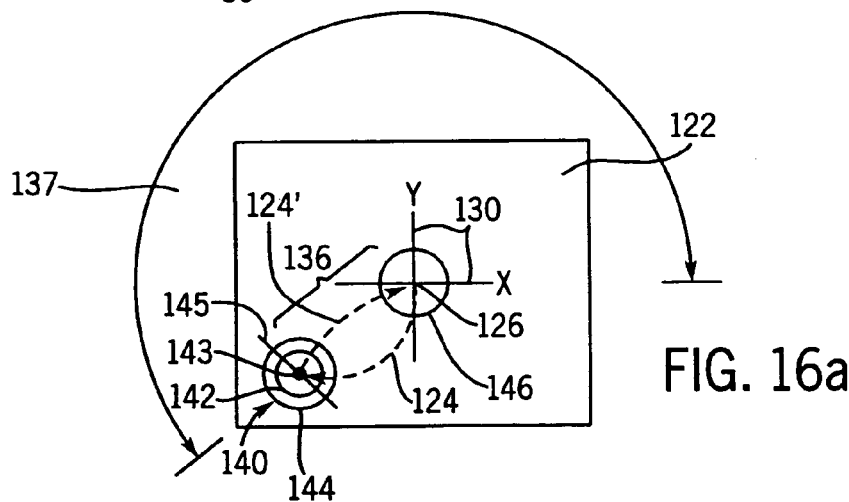
FIG. 16a
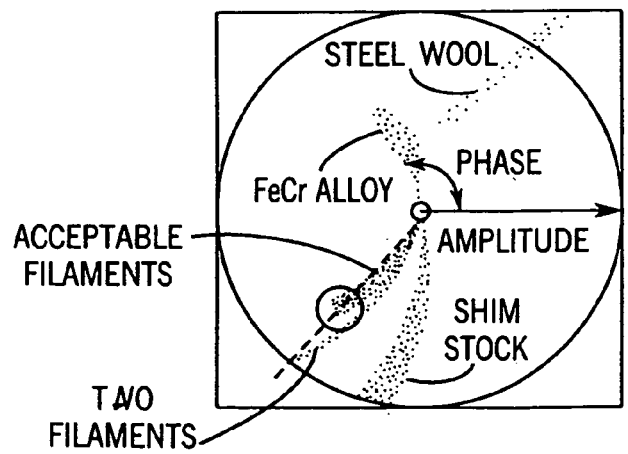
FIG. 16b

DETECTOR FOR MAGNETIZABLE MATERIAL USING AMPLITUDE AND PHASE DISCRIMINATION

CROSS-REFERENCE TO RELATED APPLICATIONS

This application is a continuation of utility application Ser. No. 10/012,939 filed Dec. 10, 2001, now U.S. Pat. No. 6,937,011, entitled "Detector for Magnetizable Material Using Amplitude and Phase Discrimination" and claims the benefit thereof.

BACKGROUND OF THE INVENTION

The present invention relates to a detector system for identifying among multiple magnetizable markers that may be embedded in other materials for sorting, authenticating, and/or sensing operations.

In the manufacture of a multi-component product, for example, packaged pharmaceuticals intended for over-the-counter sale, it is important to verify that the package includes a paper insert listing the characteristics of the drug and instructions for safe use. While considerable care is taken in placing the insert into the package, ideally, its presence in the package could be verified after the package is sealed. One way of doing this is by weighing the package to detect the additional weight of the insert. For light inserts or products that vary in weight, such an approach is unreliable.

The grandparent to the present application describes a method of verifying the presence of a component of a manufactured product by incorporating a small amount of filamentized magnetic material into that component, the latter whose presence may be detectable at a distance. The filaments are of low cost and may be freely dispersed into the material of the component for manufacturing convenience and may be remotely sensed even through packaging or the like. Unlike "magnetic stripe" type techniques for recording data, this invention allows identifying the component without direct contact.

While the ability to sense an individual component in a manufactured product is valuable, often it may be necessary to sense combinations of components or to distinguish between different component types. The parent to the present application describes a method of communicating not simply presence or absence of a component in an assembly, such an operation that requires only the conveyance of a single binary "bit" of information, but of distinguishing between different components containing different types of magnetizable filaments, each conveying one bit of multiple bits of information.

The number of different types of magnetic filaments that can be distinguished using previous techniques is limited. What is desired is an improved detection technique that allows a large number of different components to be distinguished from one another using magnetic marking techniques.

BRIEF SUMMARY OF THE INVENTION

The present inventors have recognized that additional data may be extracted from the interrogation of magnetic filaments and other markers by capturing both amplitude and phase of the magnetic field induced in the markers. A phase-amplitude space may be divided into many distinct regions each of which may describe a unique combination of filament types and quantities, including mixtures of filament types. Further, an additional dimension of discrimination may be obtained by observing a phase-amplitude trajectory as the applied magnetic field is changed in effective strength, either directly, or as the indirect result of the materials carrying the magnetic markers moving into and out of the field region. In this way, a greater number of marked components may be successfully distinguished or single or multiple components authenticated.

Specifically, the present invention provides a detector system for magnetizable materials. The detector system includes an electromagnet coil adjacent to a volume sized to receive at least one type of magnetizable material. The coil produces a time-varying magnetic field having a first frequency component. A detection antenna adjacent to the volume detects time dependent variations in the magnetic field caused by the introduction of magnetizable material into the volume. Signal processing circuitry determines the amplitude and the phase of the magnetic field variation with respect to the first frequency component and amplitude of the magnetic field variation to provide an output signal dependent upon a predetermined classification of the amplitude and amplitude and phase into ranges.

It is thus one object of the invention to increase the amount of data that can be extracted from items marked by magnetizable materials. By capturing both amplitude and phase, better discrimination between material types may be had and a wider range of different marker types may be created using mixtures with different quantities of different magnetic material types.

The time varying magnetic field may also vary (as measured at the magnetic material) at a second frequency component lower than the first frequency component and the signal processing circuitry may determine amplitude and phase for a sequence of times during a period of the second frequency component to produce a phase-amplitude trajectory. In this case, the output signal may be a function of the path of the phase-amplitude trajectory entering and exiting the predefined ranges.

Thus it is another object of the invention to obtain yet additional information about the markers based on dynamic changes in amplitude and phase as the overall intensity of the magnetic field increases and decreases.

The predetermined range may be described by an inner and outer boundary and the output signal may require that the phase-amplitude trajectory pass into the inner boundary prior to setting the output signal and pass out of the outer boundary prior to resetting the output signal.

Thus, it is another object of the invention to provide hysteresis in the changing of the output signal so as to prevent signal fluctuation at the edges of a predefined range.

The magnetizable material may move with respect to the coil so as to create the variation of magnetic field at the second frequency component or the electrical power to the coil may be varied to create the second frequency component.

Thus it is another object of the invention to provide variation in the magnetic field needed to provide an added dimension of discrimination either through the movement of product on a conveyor belt or the like past the detection antenna and coil or by manipulation of the coil voltage directly for reading of stationary items.

Multiple predetermined ranges may be created to provide separate output signals where the ranges differ by amplitude range.

Thus, it is another object of the invention to be able to discriminate between different materials by the quantity of marker introduced into the detected component or the amplitude of the output signal.

Filaments of different magnetic materials may be incorporated in a single component of a product in different amounts so that a variety of different components provide different amplitude and phase.

Thus, it is another object of the invention to be able to encode information into an object by using a variety of magnetic filaments and different amounts and subsequently reading that encoded information.

Alternatively, the multiple output signals may be provided by predetermined ranges having a different phase angle.

Thus, it is another object of the invention to provide for distinguishing between components by use of different magnetic materials having different phase properties or by mixtures of different materials to create composite phase angles differing from the phase angles of either of the materials.

More generally, the output signal may require the passing of the phase-amplitude trajectory in predetermined order to at least two predefined ranges.

Thus, it is another object of the invention to provide for the detection of complex phase-amplitude trajectory behavior as may be incident to some materials or mixtures.

The signal processing circuitry may determine amplitude and phase with respect to the second frequency component.

Thus it is another object of the invention to provide yet another dimension of discrimination when the position of the magnetizable materials are known for the amplitude and phase to be used to determine the type and absolute amount of magnetizable material.

The output signal may indicate an amount of one species of magnetizable material or an amount of multiple species of magnetizable material, or relative proportions of multiple species of magnetizable material and magnetizable species of material.

Thus, it is another object of the invention to provide extremely flexible output signals for different applications of the inventive technique.

The detector may further include a display plotting amplitude and phase of the signal over the course of at least one cycle of the second frequency component and a drawing tool for drawing at least one region on the display over the plotted phase-amplitude trajectory so as to input a range of amplitude and phase of predefined range on the display. Alternatively, the region may be determined automatically based on the statistics of reference samples Thus, it is another object of the invention to provide a means of teaching the detection system of the present invention to recognize particular combinations or types of magnetizable material on-site such as accommodates possible variations caused by local site environment or component environment.

The foregoing and other objects and advantages of the invention will appear from the following description. In the description, reference is made to the accompanying drawings, which form a part hereof, and in which there is shown by way of illustration a preferred embodiment of the invention. Such embodiment does not necessary represent the full scope of the invention, however, and reference must be made to the claims herein for interpreting the scope of the invention.

BRIEF DESCRIPTION OF THE SEVERAL VIEWS OF THE DRAWINGS

FIG. 1 is a perspective view of an assembly line in which a product including material of the present invention is enclosed in a package and later remotely sensed by a sensing device of the present invention;

FIG. 2 is a perspective view of example uses of material of the present invention including a package cap, label, and instructional insert;

FIG. 3a is a plan view and enlarged detail showing the instructional insert of FIG. 2 having magnetic filaments dispersed within a paper matrix;

FIG. 3b is an enlarged plan view of one such magnetic filament;

FIG. 4 is a schematic diagram of the sensing device of FIG. 1 employing synchronous detection of magnetization of the filaments;

FIG. 5 is a figure similar to that of FIG. 4 showing an alternative embodiment of the sensing device employing frequency domain analysis of the total magnetization to detect saturation of the filaments of FIG. 3a;

FIG. 6 is a spectrum diagram of the output of the sensing device of FIG. 5 in the absence of material of the present invention;

FIG. 7 is a figure similar to that of FIG. 6 showing output of the sensing device of FIG. 5 in the presence of material of the present invention;

FIG. 8 is a plot of magnetic induction M vs. external magnetic field H showing the time response of the magnetic filaments during one cycle of the first frequency component and the saturation of the magnetic filaments of the material of the present invention;

FIG. 15 is a schematic diagram of an alternative version of the sensing device of FIG. 1 employing phase-amplitude detection of magnetization of the filaments;

FIG. 16a is a plot of phase-amplitude space showing phase-amplitude trajectories detectable by the sensing device of FIG. 15 moving between predefined regions;

FIG. 16b is a plot similar to that of FIG. 16a showing trajectories for different magnetic materials;

DETAILED DESCRIPTION OF THE INVENTION

Figure 9:
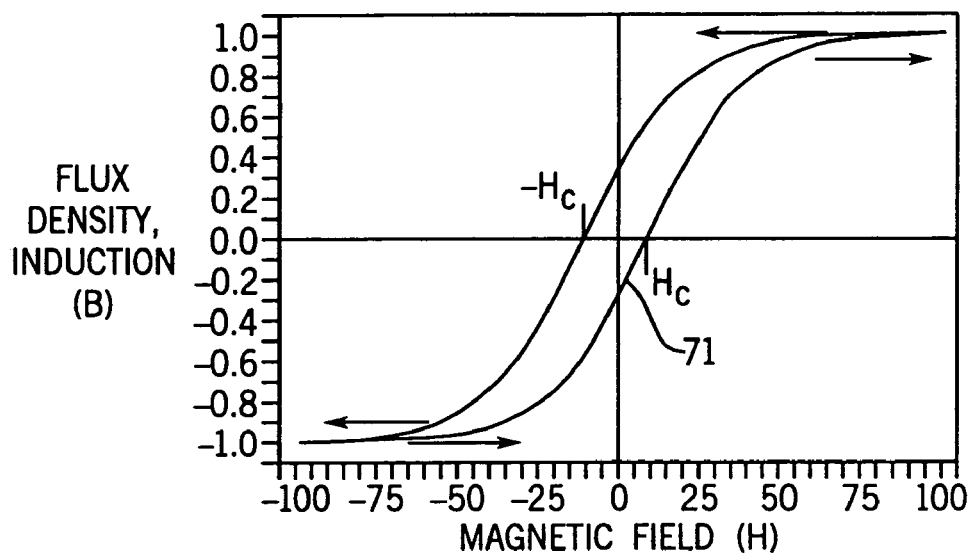
FIG. 9 is a plot similar to that of FIG. 8 showing the definition of magnetic coercivity.

Referring now to FIG. 1, an assembly line 10 may include a conveyor belt 12 transporting boxes 14 along a direction 18. At a first station 20, the box 14 may be opened and a product 16 is installed therein. With further motion of the conveyor belt 12 in direction 18, the box 14 is brought to a second station (not shown) where the box is closed and sealed.

At a third station 22, the box 14 and the product 16 contained therein pass between drive coils 24 coaxially opposed across the conveyor belt 12 perpendicular to the direction 18. As will be described below, the drive coils 24 are connected together as a coil pair for the generation of electromagnetic signals in the volume between the drive coils 24. It will be understood that the drive coils 24 may be connected in series or in parallel or may use separate properly phased amplifiers so that the magnetic fields generated by each of the coils is in the same direction and are additive (e.g., the fields positively reinforce each other). Other well-known types of sensing and excitation coils may be used. A pair of sensing coils 28 may also be positioned coaxial with the drive coils 24, but closer to the path of the box 14 on the conveyor belt 12. Alternatively as shown, four detection coils 28a-28d may be used to substantially reduce the detection of the fundamental signal from the drive coils 24. The pair 28b and 28c are arranged so that the induced voltages add. The second pair 28a and 28d are arranged so that one of the coils 28a is to the left of left coil 24 and the other coil 28d is to the right of right coil 24. They are further away from the magnetic filaments so that they do not detect them but substantially only the fundamental from drive coils 24. The four coils 28 are connected electrically such that the signals from coils 28a and 28d subtract from the signals from coils 28b and 28c reducing the first harmonic substantially to zero allowing a higher dynamic range in the detection of harmonics of the filament signals.

Alternative methods that are known in the art, such as analog or digital filtering, may be used to cancel or substantially reduce the signal component of the first harmonic. Alternatively, as will be understood in the art, the sensing coils may be replaced or supplemented with a Hall effect device, a giant- or anomalous magneto resistance sensor, a flux-gate device or any other magnetometer. These detectors may also be combined with fundamental canceling detectors analogous to coils 28a and 28d described above.

Conventional proximity sensing elements 30 such as photoelectric sensors may also be positioned along the conveyor belt 12 to detect the presence of the box 14 in third station 22 so as to activate the sensing of the box's contents, as will be described below.

Referring now also to FIG. 2, the product 16 within the box 14 may include, for example, a bottle 32 containing a pharmaceutical material. The bottle may have a resealable cap 34, a label 36 affixed to the bottle's surface, and may be packaged with a paper insert 38 providing information about the pharmaceutical material.

At different stages of the product's manufacture, it may be desirable to determine the presence of any one or all of the cap 34, label 36, and paper insert 38. Accordingly, any one or all of the materials of these elements may be treated by the incorporation of a plurality of magnetic filaments 40 into the material of the element. In the case of a cap 34, the filaments may be mixed with the thermoplastic from which the cap is molded in the manner of fiberglass and other reinforcement materials according to techniques well known in the art in which the filaments are dispersed in the liquefied plastic.

For the label 36, which for the purpose of example, may be printed directly on the bottle 32, the filaments 40 may be mixed with the printing inks. It will be understood that alternatively, the filaments could be in the label paper or adhesive. The paper insert 38 may have filaments 40 that were introduced during the papermaking process to blend and disperse with the cellulose fibers of the paper pulp. The paper may then be processed and printed by conventional means. The filaments may also be encompassed into woven, knitted, or nonwoven fabrics, cardboard, ceramic and composite wood products for other applications.

Referring now to FIG. 3a in the present example of FIG. 1, it may be desired to confirm that the paper insert 38 is within the box 14 after the box has been sealed. Accordingly, in this case, only the paper insert 38 includes the filaments 40. The filaments 40 are randomly dispersed within the paper constrained only by the thickness of the paper (causing the filaments to lie within the plane of the paper) and a degree of alignment caused by the papermaking process which aligns the fibers of the paper in a "grain" generally determined by the water flow over the Fourdrinier screens. In the present example, however, within the plane of the paper, it is desired that the filaments 40 obtain the greatest random dispersion both in location and in orientation to ensure a signal regardless of orientation of the paper insert 38 after it has been folded and placed in the box 14.

Each of the filaments 40 in the preferred embodiment is constructed of an easily magnetizable material or "soft" magnetic material of coercivity of less than 2400 amperes/meter (30 Oersted) and preferably less than 1200 amperes/meter (15 Oersted). Coercivity is the magnetic field that must be applied opposite to the magnetization direction of a magnetically saturated material that is required to reduce the magnetization to zero. Suitable materials include Permalloy, Nickel iron alloy, Supermalloy, and Fecralloy, ferritic Stainless Steel, low carbon steel; however, other similar materials may be used. The more easily the material is magnetized and the greater its saturation, the greater the signal that may be produced by the filaments 40 and the further away the filaments 40 may be detected as will be described. The material of the filaments 40 may preferably have a saturation induction from about 0.5 to 2 Tesla (5000 to 20,000 gauss) to allow them to be more readily detected. A permeability of larger than 100 is preferred. A limit on the permeability or the number of filaments, however, may be established so that the filaments 40 do not trigger anti-shoplifting devices, which may use a related principle of detecting saturation of larger foils of magnetic materials within a magnetic field.

Desirably the filaments 40 have a very high aspect ratio, the aspect ratio being a ratio between the filament's length 42 and diameter 44 (shown much exaggerated in FIG. 3b). In the preferred embodiment, lengths of 3 to 6 mm and diameters of 2 to 8 microns have been found to be achievable, however, generally aspect ratios of greater than 3 will realize some improvement in signal strength and aspect ratios of greater than 100 may be desired. The high aspect ratio decreases demagnetization effects in which the magnetic field generated inside of the filament 40 by the magnetization of the material/opposes the external magnetic field applied to the filaments 40. Thus, generally higher aspect ratios are preferred.

The size of the filaments 40 in length and diameter may be adjusted to improve their miscibility with the matrix material 41. Generally, in these cases, it is desired that the filaments 40 remain suspended and not settle from the matrix during the processing. The optimum size of the filaments 40 may be determined empirically. The small size in diameter of the filaments 40 render them invisible or nearly invisible when incorporated into paper or other materials. Filaments 40 may be clad with a noncorrosive material to prevent rusting in place in the matrix.

The matrix material 41 may be selected from a variety of non-magnetic low permeability materials including but not limited to paper, plastic, paint, ink, adhesives and thin metal films or foils such as aluminum foil. Together the filaments 40 as dispersed in the matrix material 41 produce a target material 39 whose presence may be remotely sensed.

Referring to FIG. 4, detection of the target material 39 may be performed in a number of different manners. In a first system, the drive coils 24 are connected to electrical amplifier/oscillator 48 driving the coils with a sine wave signal preferably having a value between 500 Hz and 3000 kHz to make use of audio frequency amplifier and signal processing components. It will be understood that the exact frequency may be chosen for convenience. High frequencies increase the sensitivity of the sensing coil and decrease the interference from 60 Hz harmonics from power lines and the like. The amplifier/oscillator 48, so connected, creates an oscillating external magnetic field 50(H) aligned with the axis of the drive coils 24. The target material 39 when stimulated by the magnetic field, H, 50 causes a magnetic induction field 52(B), being the result of a magnetization M of the filaments 40 (and in particular those filaments aligned approximately along the direction of the magnetic field, H, 50).

The magnetic flux density, B, 52 may be received by sensing coils 28 which measure the derivative with respect to time of the magnetic flux density, B, 52 and detected by means of a Fourier analyzer 54. The Fourier analyzer 54 computes the amplitude and phase of one or more harmonics of the signal. The output may be provided to a magnitude or threshold detector 56 to produce a signal at input output circuitry (I/O) of block 58 such as may be part of an industrial control system or the like to provide an output signal and effect a predetermined control action. The Fourier analyzer 54 detects the unique phase of the time derivative of the magnetic flux density, B, 52 to reduce the effects of environmental noise on the detection process. It will be understood that the sensing coils 28 may be another form of magnetization detection such as a Hall effect device or the like.

Referring now to FIG. 5, in an alternative embodiment of the detection system, the drive coils 24 are again attached to amplifier/oscillator 48 in parallel to generate an oscillating magnetic field, H, 50 along their axis. The sensing coil 28 may be used to detect the magnetic flux density, B, 52 from the target material 39 or alternatively the drive coils 24 may serve double duty both as transmitting and receiving antennas. In either case, a signal due to the magnetic flux density, B, may be provided to a band pass filter or a high pass filter 60 that admits only frequencies significantly above the fundamental frequency $f_o$ of the amplifier/oscillator 48. The signal from the filter 60 is introduced to an amplitude and phase detector 55 that detects the magnetic flux density, B, 52 only so far as it is at the proper phase with respect to the magnetic field, H, 50 so as to reduce the effects of environmental noise on the detection process. The detector 55 output may be provided to a magnitude or threshold detector 56 to produce a signal at I/O block 58 such as may be connected to an industrial control system or the like to provide an output signal and effect a predetermined control action. The use of a digital or analog filter, together or as an alternative to the signal subtraction described above, distortion of the waveform may be provided to a detector such as results in the introduction of higher ordered harmonics to a sine wave. It will be further recognized that other waveform distortion detection systems may be used.

In the preferred embodiment, the 5th harmonic is detected. The sensing coils 28 are connected so that the first harmonic component of the signals from coils 28b and 28c are almost completely subtracted by coils 28a and 28d. The output of coils 28 is connected to a buffer amplifier, which incorporates a low-pass anti-aliasing filter that is required by the analog to digital converter. This low pass filter does not affect the phase of the 5th harmonic as would a low frequency bandpass filter. The output of the buffer amplifier is provided to the inputs of a 24-bit sigma-delta A/D converter, which provides 24 bit digital samples at a rate of approximately 16276 Hz. This sample stream is processed using a digital signal processor to extract the phase and magnitude of the 5th harmonic. Other well-known methods for extracting the magnitude and phase of harmonics may also be used, for example, those using analog electronic components such as modulators and band pass filters. Those skilled in the art will realize that odd harmonics other than the 5th could be used.

Referring now to FIG. 8, the distortion of the magnetic flux density, B, 52 with respect to the magnetic field, H, waveform results from phenomenon of magnetic saturation of the filaments 40. The filaments 40 under the presence of the external field, H, 50 and as a function of their permeability and softness, will become magnetized in conformity with the magnetic field, H, 50 producing a greater magnetization M with increasing field H up to saturation limits 62 whereafter no further increase in magnitude of the magnetization may be had because all magnetic domains are aligned. At this point, the magnetization M reaches an upper or lower limit as indicated by plateaus 63. Since $B=4_\pi \times 10^{-7}(H+M)$, the magnetic filaments 40 cause the magnetic flux density, B, 52 to be distorted introducing the higher ordered harmonics that are detected.

Referring to FIG. 6, if the magnetic field, H, is essentially a pure sine wave, in the absence of any magnetic material, the detected magnetic flux density, B, 52 will exhibit a fundamental frequency 64 at the frequency of the sine wave and possibly a low amplitude-high order harmonics 66 resulting from imperfections in the sine wave generation. In general, there is essentially no significant harmonic content above the third harmonic.

Referring to FIG. 7, with the introduction of the target material 39 however and its saturation, odd harmonic components 68 will be introduced starting at the third harmonic and extending beyond the forty-first as shown in FIG. 7. The amplitudes will depend on the strength of the magnetization M, the magnitude of the applied field 50, and the sharpness of the rising an falling portions 61 of the magnetization curve 52. These harmonic components, isolated through the band pass filter 60 of FIG. 5 are provided to the Fourier analyzer 54, amplitude and phase detector 55 or other output device as has been described. The control system may provide an output indicating proper assembly of a multi-component product having a critical component incorporating the target material 39.

In an alternative embodiment not shown, the axis between the drive coils 24 may differ from the axis of the coil 28 to obtain off axis signal magnetic flux density, B, 52. Techniques to reduce the detection of the external field H and to enhance the detection of the local field B may include a subtraction of the signal from the amplifier/oscillator 48 in phase with the detected signal or the use of sensing coils 28 wound in opposition so as to provide a cancellation effect for the magnetic field, H, 50 positioned asymmetrically with respect to the target material 39 so as not to cancel the detected magnetization, or the coil-based subtraction technique described above, as is generally understood in the art.

Multi-Bit Detection

Referring again FIGS. 2 and 3a it may be desirable to detect all three of the cap 34, label 36 and paper insert 38. Alternatively, it may be desirable to detect among alternative versions of the paper insert 38. For these purposes, several different sets of magnetic filaments 40 having different magnetic properties may be used.

Different ones of the sets of filament 40 may be incorporated into each of the cap 34, label 36 and paper insert 38 to individually detect the presence or absence of each of these components. The number of simultaneously detectable components will be equal to the number of different sets of filaments 40.

Alternatively, different ones or combinations of the set of filaments 40 may be incorporated into the label 36, the presence or absence of each such set of filaments forming a single binary bit of a multi-bit word. The number of different combinations in a single detected component will be equal to $2^N$ where N is the number of different types of filaments 40. Alternatively, and as is rendered possible by the present invention, the amplitude and phase of the filaments may be taken into account to provide a number of analog levels that may be distinguished. Here the number of different combinations will be much greater than $2^N$ where N is the number of different types of filaments 40 because of the discrimination of amplitude and phase as will be explained below.

Referring to FIG. 9, the different sets of filaments 40 suitable for this purpose have different magnetic properties as defined by the set material's magnetization curve 71. The magnetization curve 71 shows the functional relationship between an applied external magnetic field H and induced magnetic field B. As is understood in the art, the function relating B and H is dependent upon the direction of change of the magnetic field, H, producing a hysteresis whose magnitude measured at B=0 is the material's coercivity $H_c$. Generally, in the preferred embodiment, the materials of each different set of filaments 40 will have different coercivities.

Figure 10:
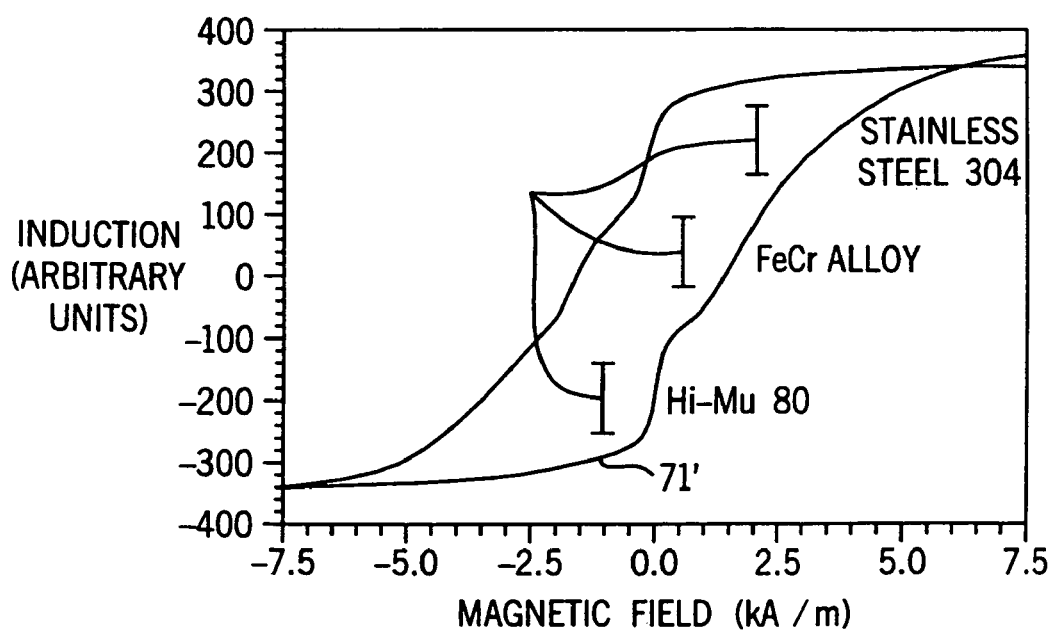
FIG. 10 is a plot similar to that of FIGS. 8 and 9 showing the effect on the hysteresis curve of the introduction of three different filaments providing three different magnetic coercivities per the present invention.

Referring now to FIG. 10, a magnetization curve 71' for a mixture of multiple sets of filaments 40 is the superposition of the magnetization curves for each different material of the different sets of filaments 40. As will be noted from inspection of the magnetization curve 71', each material provides an identifying region 75 of increased slope.

Figure 11:
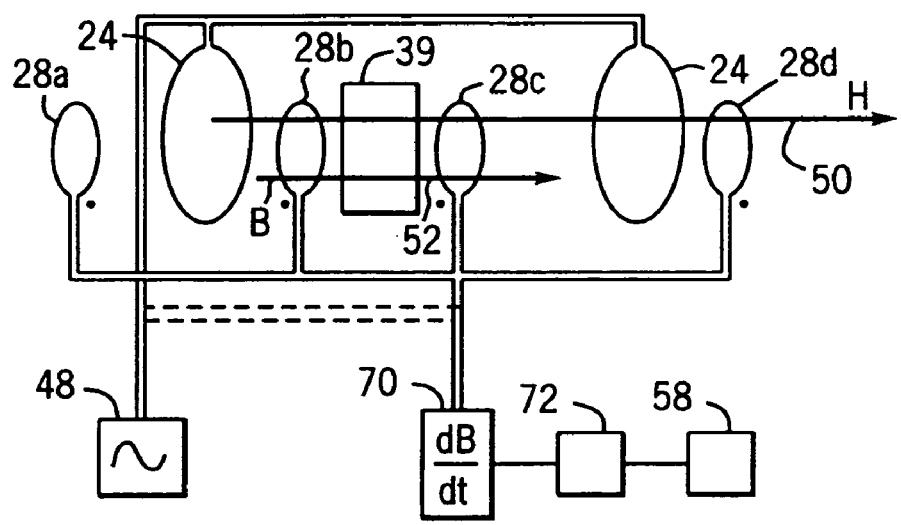
FIG. 11 is a figure similar to that of FIG. 4 showing a sensing device for detecting multiple different filaments having different coercivities and using a differentiating circuit.
Figure 12:
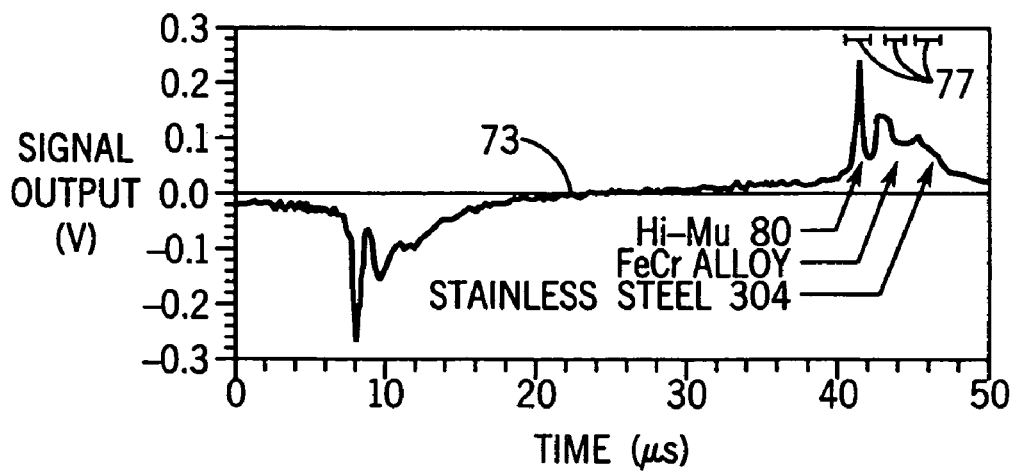
FIG. 12 is a plot of signal output from the differentiator of FIG. 11 versus time measuring a derivative of the induction units of the graph of FIG. 10 and showing multiple peaks caused by each of the magnetic filaments of the three sets.
Figure 13:
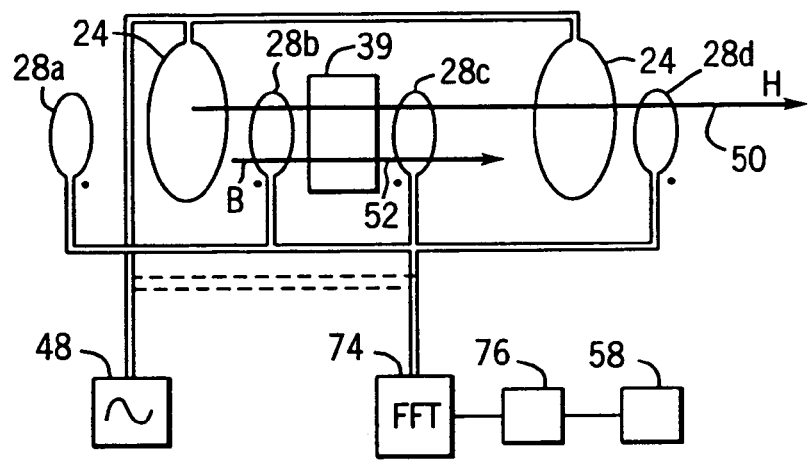
FIG. 13 is a figure similar to that of FIG. 10 showing a sensing device for detecting multiple different filaments having different coercivities and using a Fourier transform circuit.

Referring now to FIG. 11, these regions 75, and hence the materials causing them, may be detected by differentiating the signal from the magnetic flux density, B, 52 as occurs naturally from sensing coil 28 and as is indicated by differentiator block 70 to provide a derivative signal 73 shown in FIG. 12. The derivative signal 73 plotted as a function of time or of phase of the magnetic field, H 50 exhibits peaks 77 corresponding to regions 75. The presence of each of the different sets of filaments 40 may be thus detected by a phase sensitive threshold detector 72 measuring the derivative signal 73 at predetermined times that correspond to the different phases in the cycle of the magnetic field, H, 50 corresponding to the times of occurrences of the peaks 77 and comparing the derivative signal 73 at those times to predetermined empirically derived thresholds. The sets of filaments 40 providing less distinctive peaks 77 may have their relative proportions with respect to other sets of filaments 40 increased. Note that the coil 28 may serve as the receiver and the differentiator whereas other types of magnetic field sensors may require a separate differentiator Referring now to FIG. 13, an alternative detector obtains the signal of the magnetic flux density, B, 52 from sensing coil 28 and takes the Fourier transform of that signal or its derivative through Fourier transform circuit 74 to produce the Fourier transform signal 78 shown in FIG. 14. The Fourier transform circuit 74 may be realized using a digital signal processor (DSP) or the like. The Fourier transform signal may be obtained with a magnetic field, H, 52 having a frequency of one kilohertz although other frequencies are possible, too.

The asymmetry in the magnetic flux density, B, 52 induced by hysteresis causes odd harmonics in the Fourier transform to be of particular value in distinguishing the presence or absence of particular sets of filaments 40. The Fourier transform signal 78 is provided to a frequency dependent threshold detector 76 which may detect the values of Fourier coefficients of the Fourier transform signal 78 or preferably compare Fourier coefficients against each other to detect individual or combinations of sets of filaments 40 according to empirically derived values. Combinations of different sets of filaments produce destructive reinforcement which is most easily detected with the Fourier transform. Another advantage of the Fourier transform is that the range of the magnetic field, H, can be kept constant and different harmonics selected to determine the presence or absence of different components.

EXAMPLE 1

Samples of different sets of filaments 40 were prepared as mixtures of approximately 5-20 milligrams of each of one, two and three magnetic materials comprising Hi-Mu 80 (also known as Supermalloy), Iron-Chromium-Yttrium (Fecralloy) and stressed Stainless Steel 304. To precisely control the coercive field produced by the filaments 40, specific treatments were provided. The Hi-Mu 80 filaments were annealed at 650° Centigrade to obtain smaller hysteresis and to maximize sensitivity. It is noted that heating in the range of 675° to 800° Centigrade results in a smaller increase in permeability than annealing between 625° and 675° Centigrade while heating at temperatures above 800° Centigrade can result in sintering of the filaments. After annealing, the Hi-Mu 80 filaments can be cut without significant decrease in the permeability, suggesting that for production, annealing can be done at the end of the filament drawing process prior to cutting the filaments.

The Fecralloy filaments were used as stressed materials in an unannealed state. Two or more different distinct magnetic functions may be obtained with Fecralloy depending on the type of annealing process so that the Fecralloy filaments may produce two different functional relationships that may be distinguished.

As shown in FIG. 10, the Hi-Mu 80 filaments 40 had lowest coercivity providing for a quick upward rise in the magnetization curve 71' with increasing magnetic field, H, 50 followed by the effect of the Fecralloy alloy and then by the Stainless Steel 304 filaments. Thus in FIG. 12 the first peak is produced by the Hi-Mu 80 filaments, second by the Fecralloy filaments and the third by the Stainless Steel 304 filaments.

Figure 14:
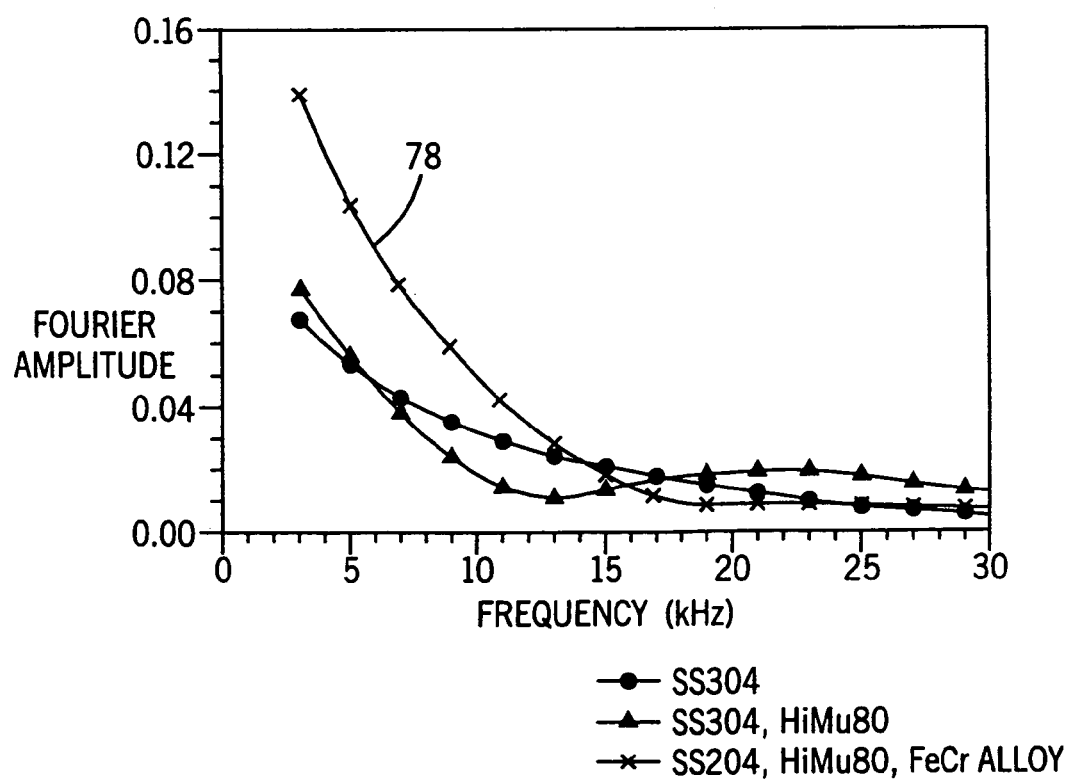
FIG. 14 is a plot of the output of the Fourier transform circuit of FIG. 13 for different combinations of the three filament types of FIG. 10.

In FIG. 14, a combination of the three filament types is shown by a Fourier transform signal 78 plotted using triangular data points. The Fourier transform signal 78 produced by a combination of the Stainless Steel 304 and the Hi-Mu 80 filaments 40 is plotted using rectangular data points. A Fourier transform signal 78 produced by only Stainless Steel 304 filaments is plotted using circular data points.

Measurements of the Fourier transform signals 78 shown in FIG. 14, at nine and nineteen kilohertz will accurately define the mixture.

The above description has been that of a preferred embodiment of the present invention. It will occur to those that practice the art that many modifications may be made without departing from the spirit and scope of the invention. For example, because the filaments respond primarily in one direction, three orthogonal coils could be used for detection and/or excitation of the filaments. The coils would be electrically isolated because of their orientation but could also be sequentially activated or distributed along a conveyor belt or the like to further minimize interference. Another embodiment is to use analog circuitry rather than a Fourier transform to discern different peaks as shown in FIG. 12.

Fourier Transform Phase-Amplitude Detection

Referring now to FIG. 15, a more sophisticated detection system may make use of a digital signal processor (DSP) 80 communicating through digital to analog converter 82 to the input of a power amplifier 84 the latter which provides a sine wave output to one or more drive coils 24 configured as described above.

The DSP 80 implements a signal generator 94 providing a cosine wave output 96 adjusted to match the resonant frequency of the resonant tank circuit including drive coils 24 a series tuning capacitor (not shown) to create a resonant circuit and associated stray and tuning capacitances and inductances. The cosine waveform is provided to a low-noise power amplifier to generate the magnetic field produced by drive coils 24. In a preferred embodiment, the tank circuit is resonant at 1 kHz. At resonance a much greater voltage (Q times the amplifier output voltage) exists across the coils thus greatly reducing the cost of the power amplifier 84 over that of a non-resonant circuit. Because the circuit is tuned, tracking the signal is necessary since the values of capacitances and inductances can vary due to manufacturing tolerances and temperature dependencies.

The voltage output of the power amplifier 84 is squared, passed through a low-pass filter, and the square root is taken to create feedback signal 86. Feedback signal 86 is then the root-mean-square voltage that drives the drive coils 24. This signal is then digitized by an analog-to-digital converter 88 and provided to an envelope detector 100 that produces an amplitude 102. A signal generator 108 produces a reference amplitude 106. The signal amplitude 102 is subtracted from the reference amplitude 106 by adder 104. The output of adder 104 is provided to the variable gain amplifier 98.

The cosine wave output 96 from the digital signal processor 94 is received internally by variable gain amplifier 98 (realized within the DSP 80 as a multiplier) to provide a digital word to the digital to analog converter 82. The variable gain amplifier 98 receives as a second input an error signal produced by adder 104, which subtracts an amplitude 102 of the digitized feedback signal 86 from a reference signal 108. In a first embodiment, the reference signal 108 is a constant value however in a second embodiment, it may be a regularly varying signal such as a triangle or sine wave. The amplitude 102 of the digitized feedback signal 86 is determined by envelope detector 100, receiving the output from analog-to-digital converter 88, and extracting its envelope according to well-known techniques. Adder 104, envelope detector 100, and reference signal 108 are implemented using standard functions of the DSP 80. Detection coils 28, near the drive coils 24, provide a detected signal as described above, the detected signal being the derivative of the electromagnetic signal emitted by coil 24 as modified by induced magnetic fields from magnetic markers and other environmental sources. The detected signal is received by detection amplifier 90 and provided to second analog to digital converter 92 which produces a digital value input to the DSP 80. The detection coils 28 may be implemented and positioned as described above.

The detected signal from coil 28 is received by multipliers 110 and 112 as also implemented in the DSP 80. A second input to multiplier 110 is provided with sine wave 114 at an odd harmonic of the frequency of and the same phase as cosine wave 96 and the second input to multiplier 112 is provided with sine wave 116 also at an odd harmonic of the frequency of sine wave 96 In the preferred embodiment the fifth harmonic is used.

As will be understood in the art, the output from the multipliers 112 and 110 will include sum and difference frequencies and may be filtered by corresponding filter/envelope detectors 118 and 120 so as to extract the real and imaginary parts of the fifth harmonic of the detected signal from coil 28. The filter/envelope detectors 118 and 120 following the outputs of multipliers 112 and 110 extract the difference frequencies and perform an envelope detection as to amplitudes of the real and imaginary components of the fifth harmonics of the detected signals. The multipliers 112 and 110 and the filter/envelope detectors 118 and 120 can also be implemented in the DSP 80. Using digital signal processing in this way implements a demodulator. The selected odd harmonic is modulated by a function of the proximity of the target to the sense coils 28. The demodulated signal produced by filter/envelope detectors 118 and 120 contain the proximity function and phase information that indicate the material type.

The outputs of the filter/envelope detectors 118 and 120 may be provided as abscissa and ordinate inputs to an electronic display 122 to plot these outputs as a phase-amplitude trajectory 124 with respect to an origin 126 representing zero amplitude of the real and imaginary part at the selected odd harmonic. This trajectory is caused by the movement of the product 16 in the field created by the drive coils 24 but may also be created in a stationary product 16 by slowly varying the amplitude of the sine wave magnetic field generated by the coil 24 using a varying reference signal 108 such as mimics the change in field seen by a moving product 16 when the product 16 is in fact still.

Referring now to FIGS. 15 and 16, the electronic display 122 may be implemented as part of a standard desktop computer and may execute a stored program to display Cartesian coordinate lines 130 intersecting at an origin 126. For example, the horizontal (x) represents the real part of the harmonic and the vertical (y) represents the imaginary part of the harmonic. With motion of the product 16 past the coil 28, a real-imaginary amplitude trajectory 124 may be drawn depicting evolution with time of the real and imaginary amplitudes of an odd harmonic. In the example of FIG. 16a, the trajectory moves from the origin 126 outward along an angle 134 defining a phase angle, and by a distance from the origin 136 describing an amplitude. A circular region 140 may be displayed on display 128 marking the terminus of the trajectory 124 caused by a particular quantity and or mixture of magnetizable marker materials.

The placement of the circular region 140 with point 143 representing the center may be determined empirically by operating the invention with actual product 16 passing the drive coils 24 and 28 and observing the real-imaginary amplitude trajectory 124 and manually placing the region 140 on the screen through the use of a cursor control device 121 associated with the display 128 (as shown in FIG. 15). Entry of the trajectory 124 into the region 140 may be detected using standard graphical techniques and used to develop an output signal 135 for presence sensing applications. It will be recognized that this empirical training, in which the trajectories of known marked products 16 are observed and regions drawn on the display 122 in response to known products above, allows accurate detection of magnetically marked product 16 whose trajectories are distorted by environmental magnetizable materials.

Alternatively, other methods for setting region 140 can be used, for example, self-teaching. In self-teaching a number of different targets that represent the packages 16 are passed through detection coils 28. The maxima of the real and imaginary components of the signal are stored for each of the targets. The size of the regions 140 may be a predetermined range about the mean value, may be set manually, or may be computed using the scatter of the data points using statistical methods known in the art, for example based on statistical distribution such as the standard deviation. The self-teaching process can be initiated by computer control or through a learn command programmed into the digital signal processor. The latter method does not require a display device.

Figure 17:
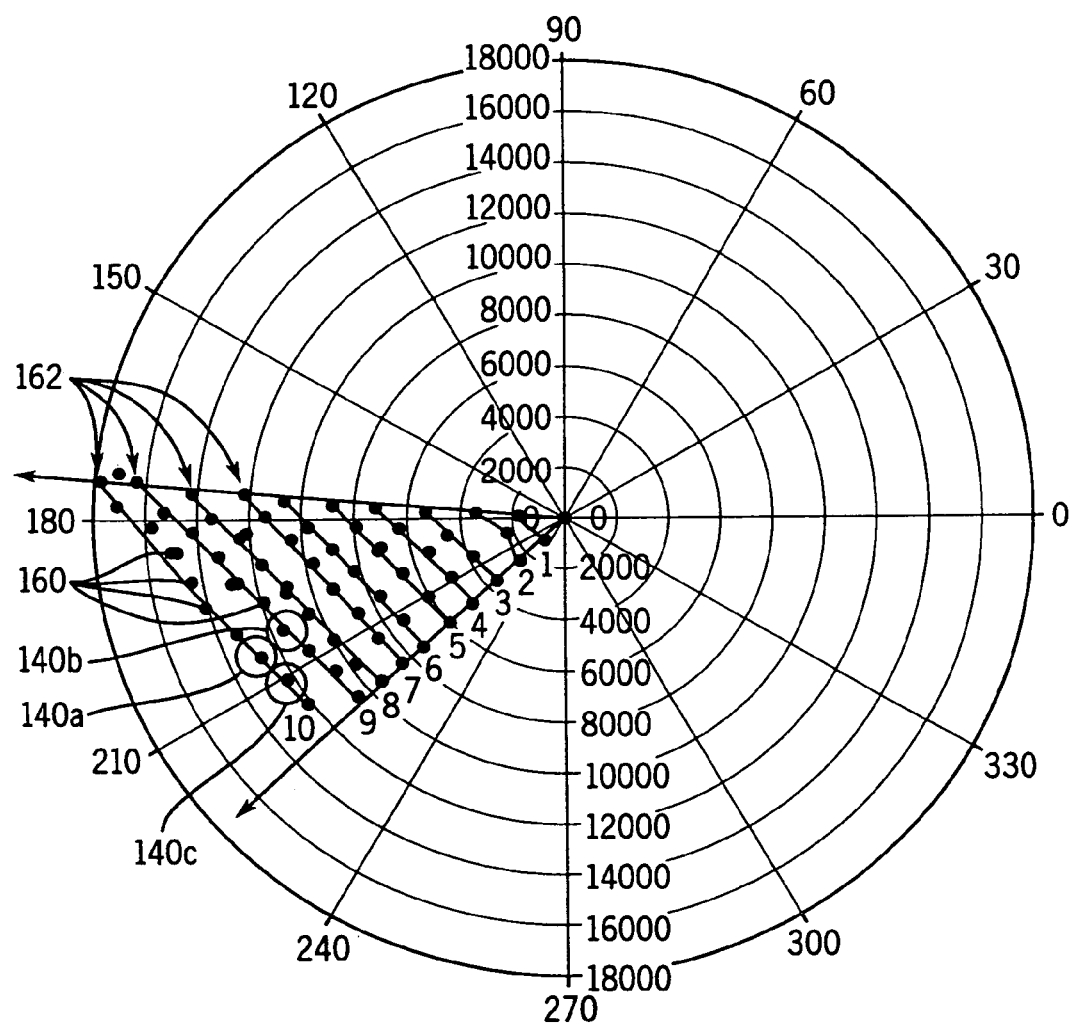
FIG. 17 is a figure similar to that of FIG. 16 showing multiple predefined phase-amplitude regions differing by amplitude and phase.

Referring to FIGS. 15 and 17, many such regions 140 may be defined, each triggering a different output signal 135 when the trajectory 124' enters into their areas so as to allow the discrimination among an arbitrarily large number of different products having magnetic markers with unique trajectories 124'. A region 140a may differ from another region (e.g., 140b) in amplitude or may differ from another region (e.g., 140c) by a phase angle or by combinations of angle and amplitude.

Referring again to FIG. 16, in one embodiment the region 140 may include an inner region 142 and an outer region 144 depicted as but not necessarily being concentric circles. A given output signal 135 may be triggered (set) only once the trajectory 124 passes into the region 140 through the inner region 142 and reset only after the phase-amplitude trajectory 124' passes out of the outer region 144. In this way, a hysteresis is created to prevent rapid change in the output signal 135 when the phase-amplitude trajectory 124 crosses a single boundary. Alternatively, an origin boundary 146 may be created about the origin 126 that may be used to reset a given output signal 135 (or all output signals) when phase-amplitude trajectory 124 passes inward through the origin boundary 146.

In a preferred embodiment, two circles 142 and 144 define two circular regions in the display. For example: circles 142 and 144 are concentric with the point 143. Circle 144 is twice the diameter of circle 142. Circle 144 is coincident with region 140. Lune 145 is one-half of circle 144 with its curved part facing the origin 126. The digital signal processor 94 detects the four states of the trajectory 124 using well known techniques to trigger a positive output for a fixed time interval that depends on the speed of product 16 on conveyor belt 18: (1) outside of region 140; (2) inside the lune 145; (3) inside circle 142; (4) outside circle 142. Any other sequence does not provide a positive output. This sequence ensures that trajectory 124 enters region 140 from the side facing the origin 126 and exits on the side facing the origin 126. If, for example, a different trajectory (not shown) passes through region 140 on its way to another region with greater magnitude (not shown) a positive output for the region with the smaller amplitude will not be triggered. The trajectory from the origin to a target region with a magnitude greater than 140 but a different phase might still pass through region 140 because the trajectories are in general continuous curves rather than straight lines.

Referring to FIG. 16a, the same trajectories and setting for region 140 can also be described in terms of a polar coordinate system where the radius from the center of the display represents the amplitude of a given harmonic and the angle relative to the horizontal line between the center and the edge represents the phase angle of that harmonic. The transformation between the Cartesian and polar coordinate system is well known in the art. FIG. 16b shows that the amplitude and phase of the fifth harmonic differs among different fibers or sheet magnetic materials.

It will be recognized that mixtures of magnetic materials having different intrinsic phase angles will create a composite magnetic material having a phase angle corresponding to a vector sum of each of the phase angles of the constituent materials weighted by their relative proportion. In this way, phase angle may be used to distinguish ratio of different magnetic materials regardless of their absolute concentrations or knowledge about the absolute magnetic amplitude at which they are excited. On the other hand, in a more controlled environment where the absolute magnetic amplitude at which magnetic markers are exposed is well controlled, both phase angle and amplitude may be used. In this case, the present invention allows different effective markers to be created simply by changing the density of the magnetic materials and detecting them using regions (e.g., 140a and 140b) that differ only in amplitude.

If the position of the product 16 or the phase of reference signal 108 is well known, it may be used to derive yet another dimension of discrimination between magnetic markers represented as a dimension normal to the display of FIGS. 16 and 17 driven by the phase of reference signal 108 or the motion of product 16. Such a three-dimensional phase-phase-amplitude space could allow additional discrimination among marked objects.

Referring now to FIG. 17, the potential resolution obtainable in the present invention is illustrated by a series of points 160 plotted in polar coordinates and arranged along lines 162 numbered from one to ten. Each point 160 represents a sample made up of various combinations of up to nine small sheets of paper (A) containing annealed HyMu 80 filaments, and up to ten small sheets of paper (N) containing non-annealed HyMu 80 filaments. The points represent the amplitude and phase of different combinations and numbers of sheets of paper N and A. Line 1 connects two points, one representing one A and the other representing one N. Line 2 connects three points representing, respectively, two A, one N and one A, and two N., Line 3 connects four points representing, respectively, three A, two A and one N, one A and two N, and three N and so forth.

As will be understood to those of ordinary skill in the art, the ability to effectively create many uniquely distinguishable magnetic markers can be used to authenticate one or more products as opposed to identifying among different products in so far as the exact amplitude and phase signature of the marker in a given reading environment may be extremely hard to reproduce through reverse engineering. Thus, the present invention is equally applicable to authentication methods.

It will be understood from the above description that the fifth harmonic is arbitrarily selected and that other harmonics may also be used and that multiple harmonics may be analyzed and mathematically combined by a sum and weighting method or other similar technique. Further, the regions 140 need not be circular, but may be pie-shaped or may be of other arbitrary size and shape providing a conforming region to a particular phase-amplitude trajectory for example. While the implementation of the invention using a DSP 80 and the interface electronics 82 through 92 represents a preferred embodiment, the functions of the invention may be arbitrarily divided between hardware and software elements according to techniques well known in the art and in fact may be implemented wholly in discrete circuitry or the like.

Figure 18:
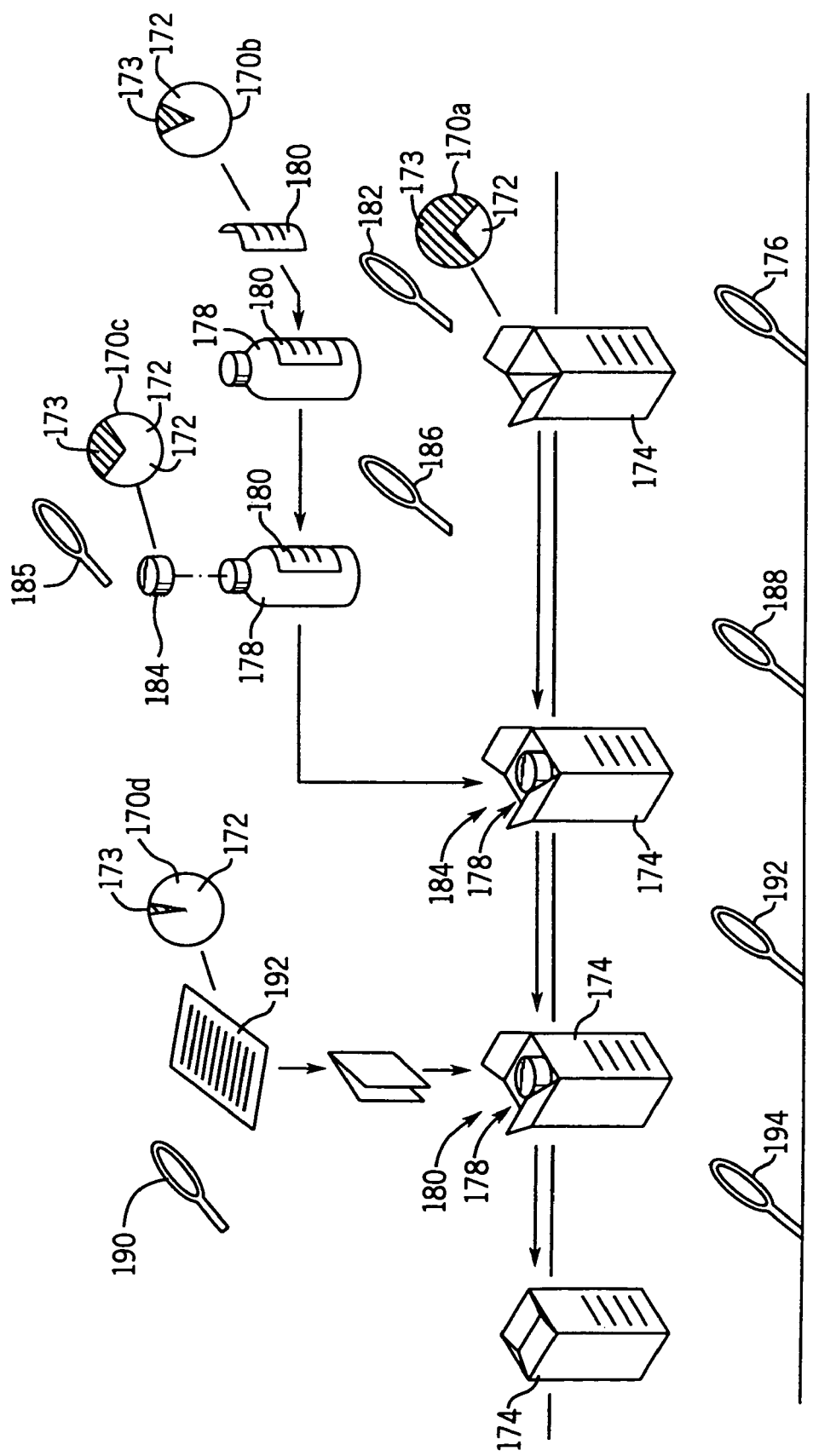
FIG. 18 is a diagrammatic flow chart of a multiple component product being assembled using the present invention.

The ability to discriminate between amplitude and phase of the magnetic filaments allows for the assembly of more complex products having detected components exceeding the number of species of filaments. For example, referring to FIG. 18, a number of different packaging components may be tagged with different ratios of two species of magnetic filaments.

First, a outer cardboard package 174 may be tagged with a first ratio 170a of the magnetic filaments 173 and 172 either contained in the cardboard of the package 174 or on a label adhered to or printed on the package. A first sensor/proximity coil 176 including a drive coils and sensor coil (as described above) and a means for determining the location of the product (such as a video camera or other proximity sensor) is positioned local to the package 174 alone, to make a phase and angle measurement of the taggant of that package 174 to confirm that the package 174 is the correct component for the assembly and to establish that the phase and angle of the taggant are within a suitable tolerance for measurements of later assembly stages.

Simultaneously, a product bottle 178 may have a taggant incorporated into its label 180 or, in fact, incorporated into the bottle 178 itself or painted on the bottle, the taggant composed of a ratio 170b different from 170a and thereby distinguishable by a second sensor/proximity coil 182 reading only the bottle and label at a predetermined distance as it passes through the assembly process.

At a later stage, the bottle 178 may have a cap 184 fitted to it, the cap being tagged through the inclusion of magnetic filaments in the plastic of the cap with yet a different ratio 170c of filaments 172 and 173. A sensor/proximity coil 185 may be used to verify the proper filament tagging of the cap before its assembly to the bottle 178 and a different sensor/proximity coil 186 may read the combined cap 184 and bottle 178 having the label 180 thereupon to confirm that most of the cap 184 and the label 180 are in place on the bottle.

It will be understood that sensor/proximity coil 186 simultaneously reads the tagging of the cap 184 and the bottle 178 and thus is used to look for an amplitude and phase that represents the vector sum of the tag in the cap 184 and bottle 178 as weighted by the absolute amount of the filaments expected in the combination.

At a next stage, the box 174, bottle 178, and cap 184 are assembled together and a sensor/proximity coil 188 may verify by similar vector addition the inclusion of all the necessary components.

Further downstream, a sensor/proximity coil 190 may verify that a product insert 192 has been correctly tagged with yet a different ratio 170d of filaments 172 and 173 embedded in the paper during the papermaking process. The insert 192 is folded and inserted in the package 174, with the bottle 178 and cap 180, and each may be read by a coil 190 to confirm the existence of all of these components.

Because of the ability of magnetic fields to pass through many materials, the package may be sealed 174 and interrogated subsequently at a sensor/proximity coil 194 to confirm that all pieces are present. It will be understood that although the reading of amplitude and phase taken at coil 194 in itself may not be sufficient to uniquely identify four elements of a package with only two species of magnetic filaments, that this sequential operation provides such an assurance through multiple reads at multiple sensor/proximity coils.

The process may be extended to more than two different filament types, however, two is sufficient to create ratiometric differences in the tags to allow multiple items to be identified. Further the exact amplitude and phase of the combinations of the product components at the given coils may be determined empirically to simplify the process of using this with an arbitrary fabrication system. Thus, the system may be expanded to packages or other manufactured products having multiple components which must be verified beyond the number of different species of magnetic filaments that are available using the amplitude and phase decoding of the present invention.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A packaged product comprising:
a plurality of constituent package components assembled to produce the packaged product wherein at least two of the package components include magnetizable filaments of at least two distinguishable species in predetermined different ratios to enable an identification of the components based, at least in part, on the predetermined ratios using at least amplitude discrimination.

2. The packaged product of claim 1 wherein the number of constituent package components assembled exceeds the number of species of magnetizable filaments incorporated into the constituent package components.

3. The packaged product of claim 1 wherein one of the constituent package components is a box.

4. The packaged product of claim 1 wherein one of the constituent package components is an instructional insert.

5. The packaged product of claim 1 wherein the two species of magnetizable filaments are incorporated into a material selected from the group consisting of: paper, solid polymer, paint, textile, and ceramic.

6. The packaged product of claim 1 wherein the two species are inserted into the constituent package components in predetermined absolute amounts.

7. The packaged product of claim 1 wherein species are selected from the group consisting of: Permalloy, Nickel Iron alloy, Supermalloy, and Fecralloy, ferritic Stainless Steel, low carbon steel, and Metglas.

8. A method of packaging a product comprising the steps of:
(a) incorporating in each of at least two constituent package components magnetizable filaments of at least two distinguishable species in predetermined different ratios to allow the at least two species to be distinguished using at least amplitude discrimination; and (b) assembling the constituent package components together such that each constituent package component is differentiated from the other based on the predetermined different filament ratios.

9. The method of claim 8 wherein the number of constituent package components assembled exceeds the number of species of magnetizable filaments incorporated into the constituent package components.

10. The method of claim 8 wherein one of the constituent package components is a box.

11. The method of claim 8 wherein one of the constituent package components is an instructional insert.

12. The method of claim 8 wherein the two species of magnetizable filaments are incorporated into a material selected from the group consisting of: paper, solid polymer, paint, textile, and ceramic.

13. The method of claim 8 wherein the two species are incorporated into the constituent package components in predetermined absolute amounts.

14. The method of claim 8 wherein species are selected from the group consisting of: Permalloy, Nickel Iron alloy, Supermalloy, and Fecralloy, ferritic Stainless Steel, low carbon steel, and Metglas.

* * * * *